United States Patent [19]
Kirkman et al.

[11] Patent Number: 5,296,701
[45] Date of Patent: Mar. 22, 1994

[54] APPARATUS FOR INSPECTING CONTAINERS HAVING A DUAL OPTICAL TRANSMISSION MEANS, A DUAL LIGHT SENSING MEANS AND A ROTATING HEAD

[75] Inventors: James A. Kirkman, Oregon; James A. Ringlien, Maumee, both of Ohio

[73] Assignee: Owens-Brockway Glass Container Inc., Toledo, Ohio

[21] Appl. No.: 48,639

[22] Filed: Apr. 19, 1993

[51] Int. Cl.⁵ ............................................. G01N 9/04
[52] U.S. Cl. ................................ 250/223 B; 356/240
[58] Field of Search ............. 250/223 B, 551, 227.26, 250/560; 356/240, 428

[56] References Cited

U.S. PATENT DOCUMENTS

| | | |
|---|---|---|
| 3,349,906 | 10/1967 | Calhoun et al. |
| 3,687,559 | 8/1972 | Fischer |
| 4,378,493 | 3/1983 | Dorf et al. |
| 4,378,494 | 3/1983 | Miller |
| 4,378,495 | 3/1983 | Miller |
| 4,498,003 | 2/1985 | Cibis |
| 4,701,612 | 10/1987 | Sturgill |
| 4,945,228 | 7/1990 | Juvinall et al. |
| 4,959,538 | 9/1990 | Swart ................................ 356/240 |
| 5,210,399 | 5/1993 | Maag et al. ...................... 250/202 |
| 4,958,2223 | 9/1990 | Juvinall et al. |

Primary Examiner—David C. Nelms

[57] ABSTRACT

Apparatus for inspecting containers that includes an inspection head positioned for rotation about a fixed axis adjacent to a container under inspection. A light source and a camera are carried by the head for directing illumination energy onto the container and receiving energy from the container after interaction with the container. The camera is connected to interface electronics for controlling camera operation and receiving data signals from the camera. The light source, camera and interface electronics are mounted on the head and rotate continuously, with the light source and interface electronics being connected by optical commutation to external control devices.

13 Claims, 4 Drawing Sheets

APPARATUS FOR INSPECTING CONTAINERS HAVING A DUAL OPTICAL TRANSMISSION MEANS, A DUAL LIGHT SENSING MEANS AND A ROTATING HEAD

The present invention is directed to optical imaging apparatus having particular utility for inspection of containers, and more particularly to an apparatus and method for inspecting containers for commercial variations and other characteristics.

BACKGROUND OF THE INVENTION

Conventional technology for mass production of glass or plastic containers involves forming the containers in a multiplicity of molds. Various types of faults or checks, termed "variations" in the art, may occur. Variations that may affect commercial acceptability of the containers are called "commercial variations." It has heretofore been proposed to employ optical scanning techniques for inspecting such containers for variations that affect optical transmission characteristics of the containers. In U.S. Pat. Nos. 4,378,493, 4,378,494 and 4,378,495, all assigned to the assignee hereof, there are disclosed methods and apparatus in which glass containers are conveyed through a plurality of stations where they are physically and optically inspected. At one inspection station, a glass container is held in vertical orientation and rotated about its vertical axis. An illumination source directs diffused light energy through the container sidewall. A camera, which includes a plurality of light sensitive elements or pixels oriented in a linear array parallel to the vertical axis of rotation, is positioned to view light transmitted through a vertical strip of the container sidewall. The output of each pixel is sampled at increments of container rotation, and event signals are generated when adjacent pixel signals differ by more than a preselected threshold level. An appropriate reject signal is produced and the rejected container is sorted from the conveyor line.

U.S. Pat. No. 4,701,612, assigned to the assignee hereof, discloses a method and apparatus for inspecting the finish of transparent containers, particularly glass containers, that include facility for directing diffused light energy laterally through the container finish as the container is rotated about its central axis. A camera includes a plurality of light sensitive elements or pixels disposed in a linear array angulated with respect to the container axis and coplanar therewith to view the external and internal finish wall surfaces, the latter through the open container mouth. Individual elements of the camera linear array are sampled by an information processor at increments of container rotation, and corresponding data indicative of light intensity at each element is stored in an array memory as a combined function of element number and scan increment. Such data is compared, following completion of container rotation, to standard data indicative of an acceptable container finish, and a reject signal is generated if such comparison exceeds an operator-adjustable threshold.

U.S. Pat. No. 4,945,228, assigned to the assignee hereof, discloses a system for inspecting the finish of a container by directing light energy downwardly onto the container finish as the container is rotated, and receiving reflections from the container finish as a function of its structural characteristics and variations. A light source is positioned to direct light energy onto the container sealing surface as the container is held in stationary position and rotated about its central axis. A camera includes an array of light sensitive elements positioned and oriented with respect to the container axis of rotation to receive light energy reflected by the sealing surface. The camera array is scanned at increments of container rotation to develop information indicative of light intensity at each array element as a function of such increments, and commercial variations at the container sealing surface are detected as a function of such information.

U.S. Pat. No. 4,958,223, also assigned to the assignee hereof, discloses apparatus for inspecting the finish of a container as the container is rotated about its central axis. A light source is positioned to direct diffused light energy onto the container finish, and a camera is positioned across the axis of the container from the light source. The camera comprises multiple arrays of light sensitive elements positioned with respect to the camera focusing elements on a common optical plane opposed to the light source to receive non-overlapping images of the container finish spaced from each other laterally of the container axis. Information processing electronics are coupled to the camera arrays for indicating optical characteristics of the container finish as differing functions of light intensity incident on the elements of each array.

Systems of the type disclosed in the noted patents have enjoyed substantial commercial success in conjunction with cylindrical containers that are symmetrical about their axes, but are not as well adapted for use in conjunction with non-circular containers such as salad dressing bottles. A general object of the present invention is to provide an apparatus and method for inspecting containers that are adapted to operate in conjunction with containers of any shape, including both round and non-round containers, and containers of any size or geometry. Another object of the present invention is to provide an apparatus and method of the described character that are adapted for inspecting any portion of a container—i.e., either the container body, the container finish or both.

SUMMARY OF THE INVENTION

Apparatus for inspecting containers in accordance with the present invention includes an inspection head for rotation about a fixed axis adjacent to, preferably coaxial with, a container. A light transmitter and a light receiver are carried by the head and oriented for directing illumination energy onto a container disposed adjacent to the head, and receiving at least a portion of such illumination energy following interaction with the container. Information processing electronics are coupled to the light receiver for detecting commercial variations in the container as a function of the optical characteristics thereof. Rotation of the head, and of the optical transmitter and receiver carried thereby, eliminates any need for rotating the container, which may thus be held in fixed position coaxial with the axis of rotation of the inspection head.

In accordance with the preferred embodiment of the invention, a light source is disposed in fixed position adjacent to the head, and a first optical transmitter on the head is aligned with the light source for receiving illumination light energy from the source and projecting such energy onto the container. A first light sensor or detector on the head receives a portion of the light energy following interaction with the container, and generates first electrical signals as a function thereof. A second light transmitter on the head is responsive to such electrical signals for generating light energy, and a second light sensor is disposed in fixed position adjacent to the head in alignment with the second transmitter for receiving light energy generated by the second transmitter and generating corresponding second electrical signals as a function thereof. The information processing electronics is responsive to such second electrical signals for detecting commercial variations in the container. Thus, in accordance with this particular aspect of the invention, the head is continuously rotated about its axis, and all communications to and from the head components are accomplished by means of commutated light energy, thereby eliminating any need for electrical brushes or the like to transmitting signals to and from the optics on the rotating head.

In accordance with another aspect of the invention in the first embodiment thereof, interface electronics is carried by the rotating head for receiving and processing the signals from the first detector. Interface control signals generated by the information processor are coupled to the interface electronics carried by the head through a third light commutator, again eliminating any need for electrical brushes or the like. In the preferred embodiment exemplifying this aspect of the invention, the interface electronics includes an annular array of light transmitters and receivers at fixed radius with respect to the axis of head rotation. An annular fiber optic array is aligned with the array of transmitters and receivers coaxial with the axis of rotation, and is connected to the information processor. Thus, the annular fiber optic array carries bidirectional communication between the information processor and the interface electronics for controlling operation of the latter, and between the interface electronics and the information processor for transmitting signals indicative of optical characteristics of the container.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 1:
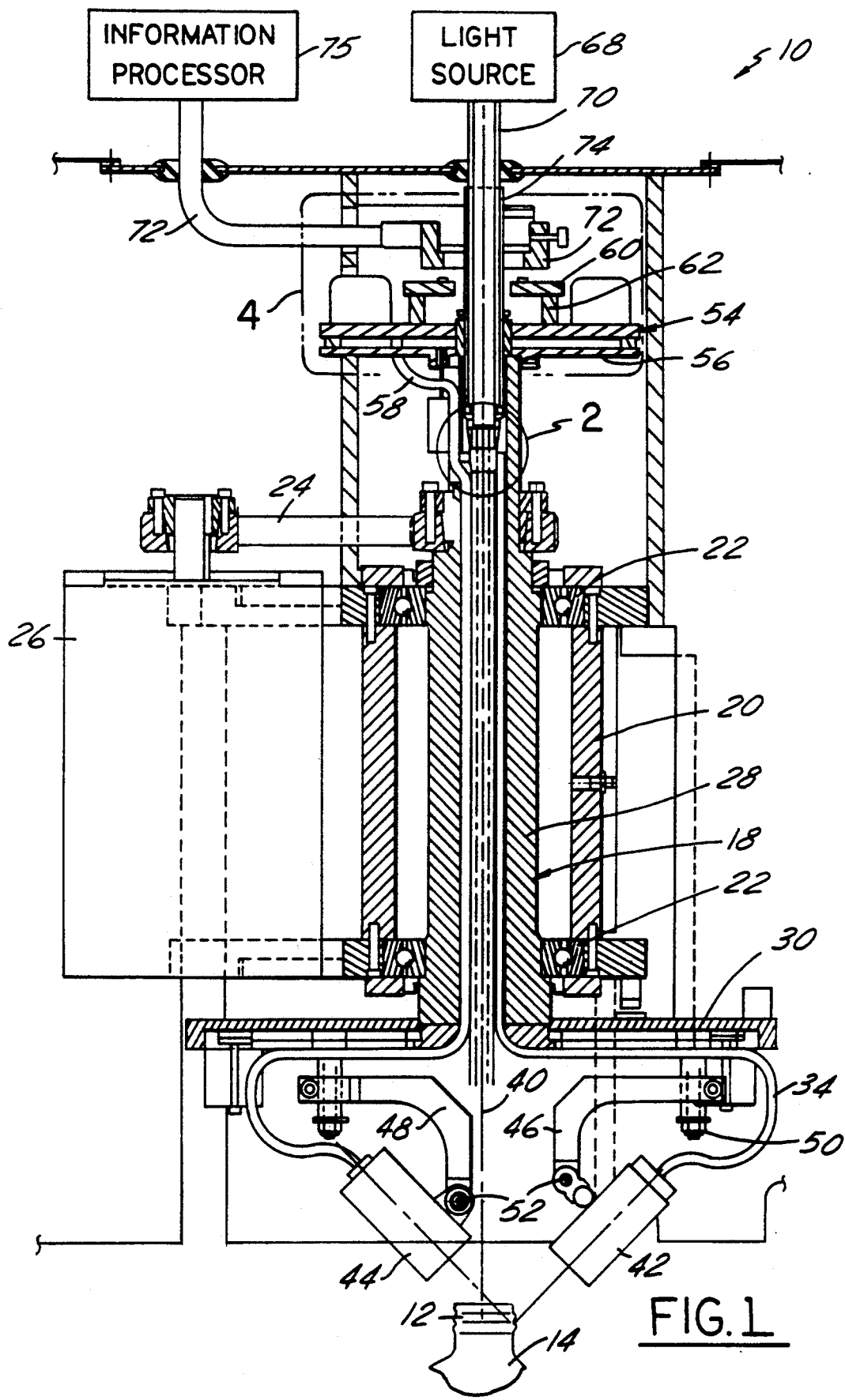
FIG. 1 is a sectional view vertically bisecting an electrooptical apparatus for inspecting containers in accordance with one embodiment of the present invention.

FIGS. 1-6 illustrate an apparatus or station 10 for inspecting the finish 12 of glass containers 14. The term "container finish" generally refers to that portion of the container that defines the container mouth. In a glass bottle, for example, the finish includes that portion of the container neck having threads and/or shoulders for receiving the container cap, as well as the upper surface of the neck surrounding the container mouth against which the cap seats and seals. Containers 14 are presented in sequence by a suitable conveyor 16 (FIG. 6), and are held stationary at station 10 during the inspection process. Presence of a container 14 at station 10 is detected by a switch or the like 17 (FIG. 7).

Figure 2:
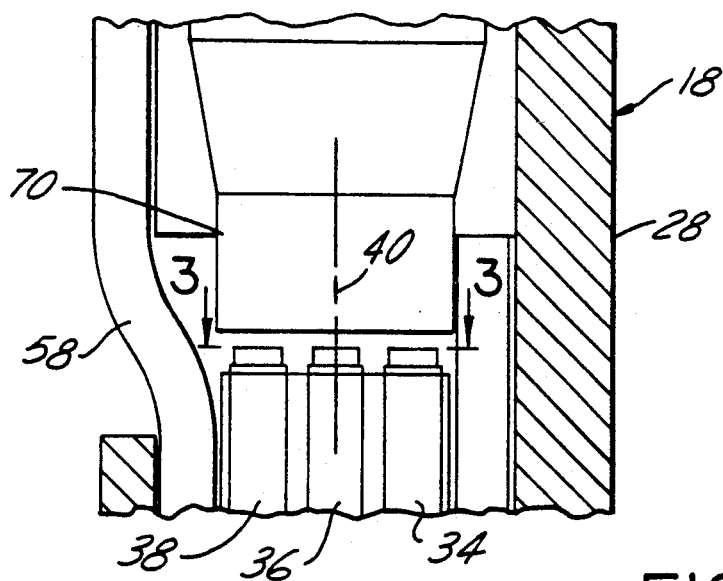
FIG. 2 is a fragmentary view on an enlarged scale of the portion of FIG. 1 within the circle 2.

The inspection apparatus includes a head 18 carried within a support bracket or collar 20 by spaced roller bearings 22, and coupled by a belt 24 to an electric motor 26 for continuous rotation at constant speed about the axis 40 of head 18. Head 18 includes a hollow generally cylindrical collar 28 carried by bearings 22, and a radially extending flange or platen 30 disposed beneath support 20. A circumferential array of up to four optical fibers 32,34,36,38 extend through the hollow interior of head collar 28. At their upper ends, and as best seen in FIG. 2, the four optical fibers 32-38 terminate in a plane perpendicular to the axis 40 of rotation. Fiber 34 extends from the lower end of collar 28 along the underside of platen 30, and is operatively coupled to a projection lens system 42 carried beneath platen 30. Fibers 32 and 36-38 are orovided for later addition of projection lenses, if desired. Fibers 32-38 may be unitary fibers, or bundles of fibers.

A camera 44 is also carried beneath platen 30. Lens system 42 and camera 44 are mounted beneath platen 30 by the respective brackets 46,48. Each bracket 46,48 is mounted by a screw 50 beneath platen 30 for angular adjustment about axis 40. Lens system 42 and camera 44 are mounted to their respective brackets 46,48 by adjustable fittings 52 for angular adjustment in planes parallel to the axis of rotation of head 18. Thus, both lens system 42 and camera 44 are fully adjustable with respect to each other and with respect to containers 12 positioned therebeneath. In the particular arrangement shown in FIG. 1, lens system 42 is oriented to direct an illumination beam onto the exterior surface of the container finish 12, and camera 44 is diametrically opposed to lens system 42 for receiving reflections and refractions from the container finish. These lens and camera orientations are by way of example only. Camera 44 may comprise a single photocell, a linear array or line scan camera, or a matrix array sensor scanned by row and column. These types of cameras are exemplified by the patents noted above, and the particular type of camera 44 employed is not per se part of the present invention.

An interface electronics assembly 54 is mounted by a bracket 56 at the upper end of head collar 28 above support 20 for rotation with the collar and head. An electrical cable 58 connects interface electronics 54 with camera 44 for conveying control signals to the camera (if required) and obtaining data signals from the camera. A circuitboard assembly 60 is mounted by stand-offs 62 above the main interface electronics board. Circuitboard 60 includes an annular or circular array of plural light emitting diodes (LED's) 64 (FIG. 5) and photosensors 66. LED's 64 and photosensors 66 are disposed in a circular array at fixed radius from the axis of rotation 40. LED's 12 are connected to interface electronics 54 for generating light signals under control of the electronics, and photosensors 66 are connected to the interface electronics for receiving and transmitting control signals to the interface electronics.

A light source 68 is disposed in suitable fixed position spaced from rotating head 18. A cylindrical fiber optic cable or bundle 70 extends from light source 68 through a fixed support collar 74 into head collar 28, and terminates in a plane spaced from and parallel to the planar ends of optical fibers 32–38. The diameter of fiber optic cable 70 is such as to overlie all of the ends of fibers 32–38, as best seen in FIG. 2. An annular fiber optic bundle 72 (FIGS. 1 and 5) is mounted by a bracket to fixed support collar 74, and opens in opposition to the circular array of LED's 64 and photosensors 66 at fixed radius from the axis of rotation. In the preferred embodiment illustrated in FIG. 1, the array of LED's and photosensors 64,66, and the annular fiber optic bundle 72, are at identical radius and axially opposed to each other. Fiber optic bundle 72 is connected to information processing electronics 75. Annular bundle 72 is of conventional type. The twelve LED's 64 and four photosensors 66 illustrated in FIG. 5 (these numbers being by way of example only) are uniformly distributed about rotation axis 40.

Figure 3:
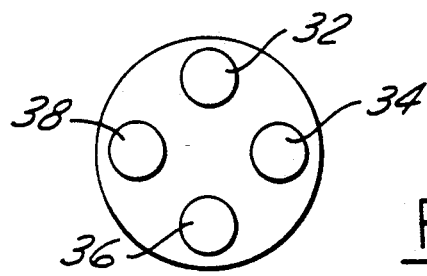
FIG. 3 is a plan view taken substantially along the line 3—3 in FIG. 2.
Figure 4:
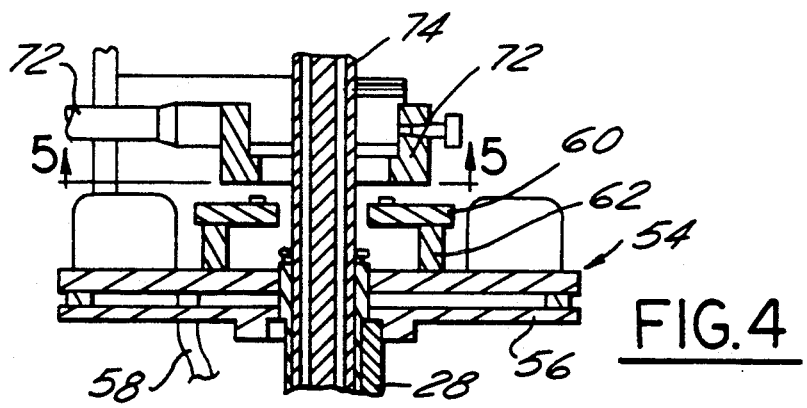
FIG. 4 is a fragmentary view on an enlarged scale of the portion of the apparatus within the line 4 in FIG. 1.
Figure 5:
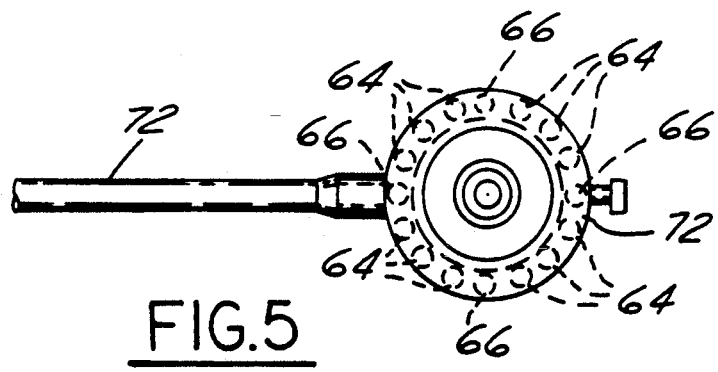
FIG. 5 is a view taken substantially along the line 5—5 in FIG. 4.
Figure 6:
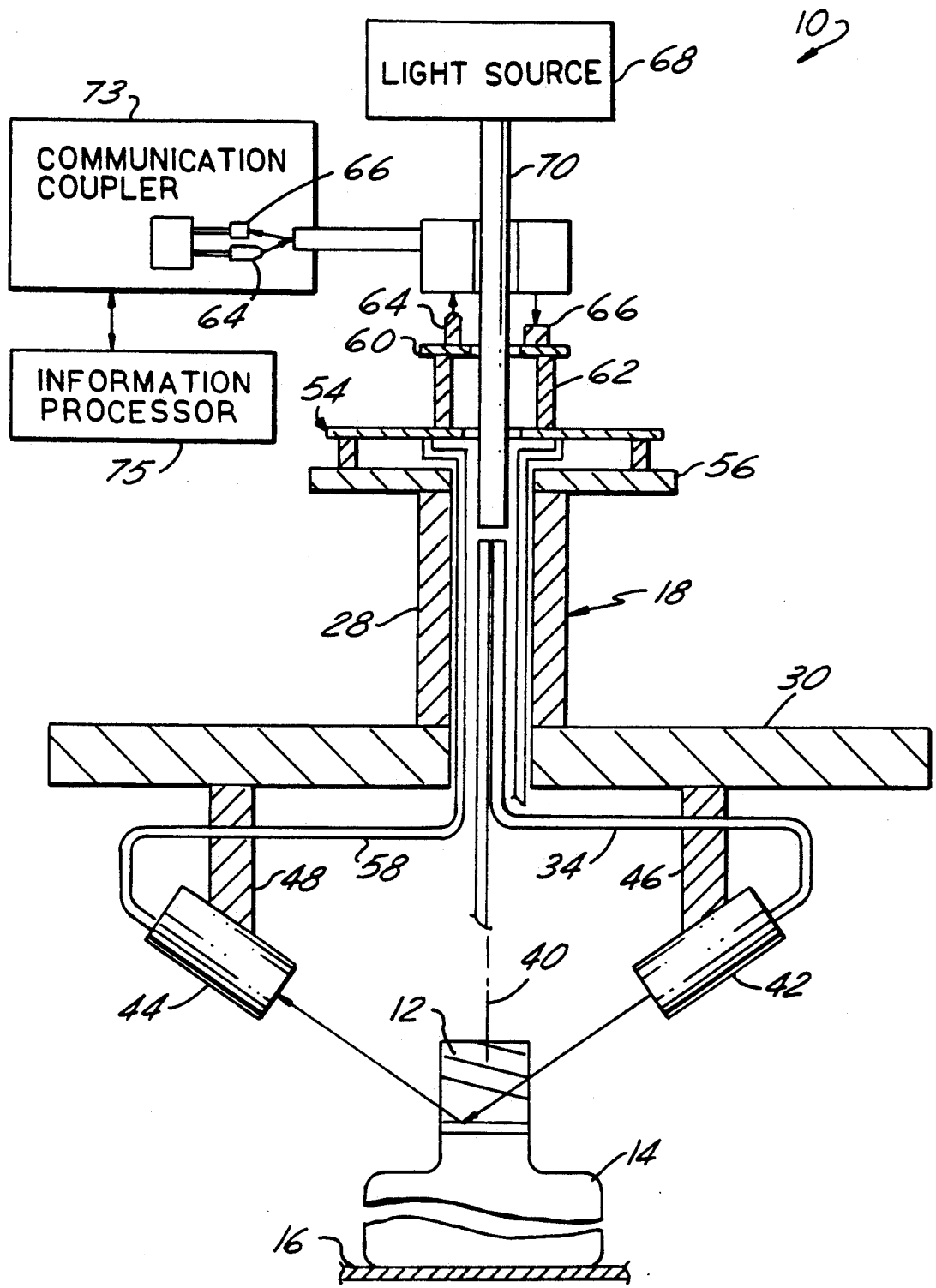
FIG. 6 is a schematic diagram of the apparatus illustrated in FIGS. 1-5.
Figure 7:
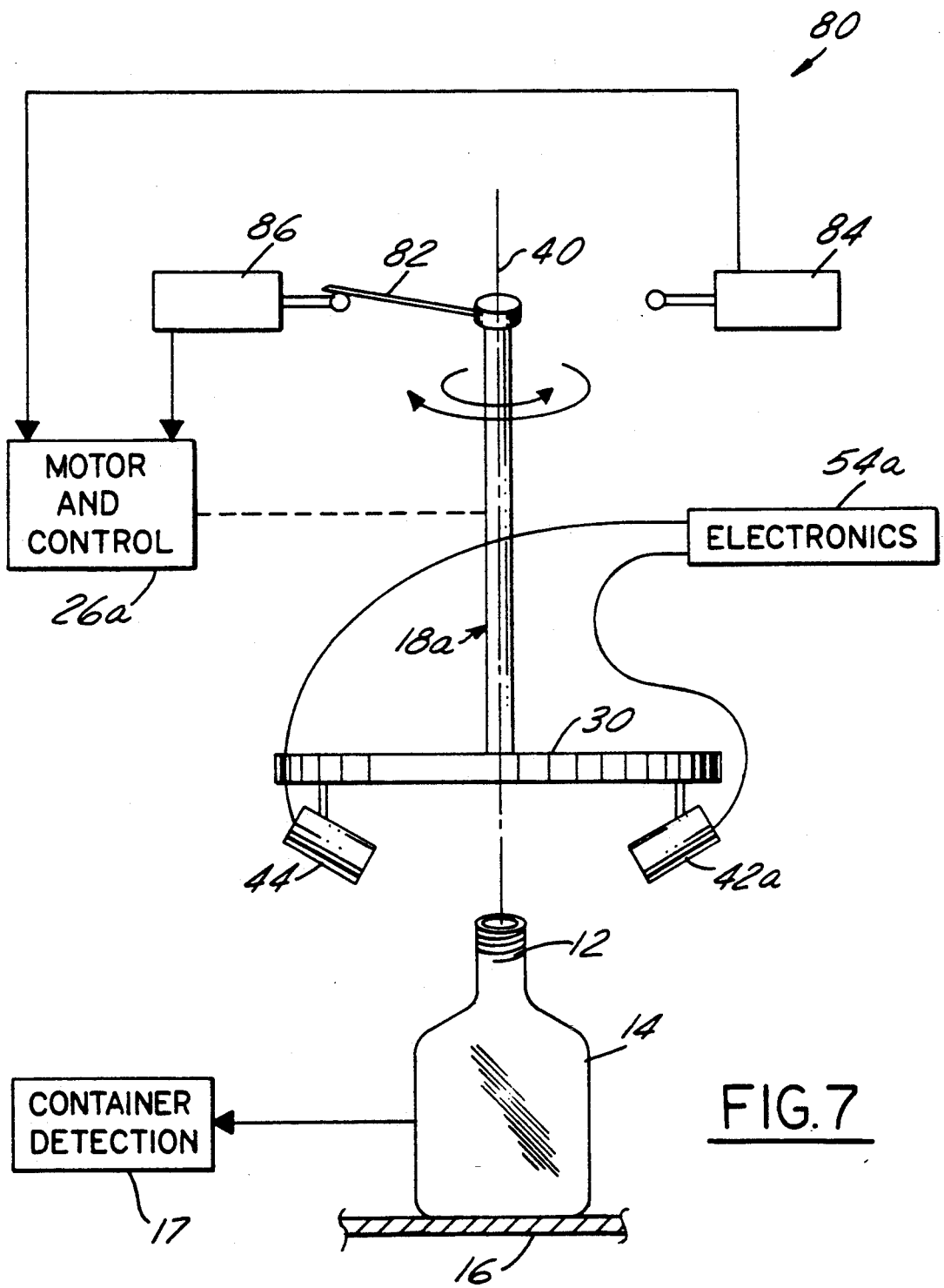
FIG. 7 is a schematic diagram of another system of the present disclosure.

In operation of apparatus 10, best illustrated in the schematic diagram of FIG. 6, containers 14 are individually transported in sequence by conveyor 16 and held in fixed position beneath head 18 coaxially with axis 40. Light from source 68 is transmitted along fiber optic cable 70 and radiated from the end thereof toward the four fiber optic bundles 32–38 (FIG. 3). Fibers 32 and 36–38 are not employed in this embodiment of the invention. Light entering the upper end of fiber bundle 34 is conducted to lens system 42, which thus receives the illumination energy from light source 68 and projects such energy onto the finish 12 of container 14. Since the radius of fiber 34 from the axis of rotation is within the overall radius of fiber 70, such transmission of illumination energy is constant and continuous independent of rotation of head 28. Camera 44 receives the illumination energy following interaction with container 14, and provides corresponding data signals along electrical cable 58 to interface electronics 54.

The interface electronics process the camera data signals as appropriate. The circular array of LED's 64 and photosensors 66 cooperate with annular fiber optic bundle 72 to provide bidirectional data communication with information processor 75 through an optical communication coupler 73. That is, information processor 75 may download control and command signals to interface electronics 54 by means of LED 64 in coupler 73, fiber optic 72 and photosensors 66 on board 60, and may receive data and other information from interface electronics 54 by means of LED's 64 on board 60, fiber optic 72 and photosensor 66 in coupler 73. In this connection, it will be appreciated that disposition of the annular fiber optic bundle in axially aligned opposition to the circular array of LED's and photosensors provides for continuous bidirectional communication (in one direction at a time) independent of rotation of head 18 and the interface electronics. This provides a number of advantages. There is no need for variable resistors, capacitors or other adjustment means on interface electronics 54. All thresholds, parameters and other control information is sent from information processor 75. This permits adjustments to be made during operation—i.e., without terminating rotation of head 18. Electronic transmission and storage of control information also avoids instabilities due to vibration or the like. Exemplary details of interface electronics 54, information processor 75, and camera control and data handling algorithms are set forth in the above-noted patents, and do not per se form part of the present invention.

FIG. 7 illustrates another system 80 in which the illumination light source 42a comprises an electronically controlled light source directly connected by suitable electrical conductors to interface electronics 54a. Camera 44 is also directly connected to interface electronics 54a, which is not mounted on head 18a. A finger 82 extends from the upper end of head 18a, and is positioned to engage at least one, and preferably a pair of angularly spaced limit switches 84,86. Limit switches 84,86 are connected to the control electronics for motor 26a.

In operation, containers 14 are again conveyed in sequence and held beneath head 18 coaxially with axis 40. Head 18a and platen 30 rotate about axis 40 back and forth between predetermined angular positions defined by the positions of limit switches 84,86 with respect to the axis of rotation. Light source 42a and camera 44 thus sweep the finish 12 of container 14 as head 18 is rotated. Since head 18a sweeps back and forth with respect to container 14, as distinguished from continuously rotating at constant speed in a given direction as in the embodiment of FIGS. 1–6, light source 42a and camera 44 may be connected directly to electronics 54a rather than through light commutation arrangements as in the previous embodiment. Limit switches 84,86 preferably are adjustable for setting the angular limits of head rotation. More than one light source 42a and/or camera 44 may be carried by platen 30. Preferably, rotation of head 18a is coordinated with intermittent motion of conveyor 16 so that head 18a sweeps in one direction for one container, stops as that container is removed and a new container is positioned, and then sweeps the second container in the reverse direction.

Although the preferred embodiments of the invention have been illustrated and described hereinabove in connection with measuring optical characteristics of the finish 12 of containers 14, it will be appreciated that the basic principles of the invention can be applied equally as well to inspection of other portions of the container, such as the container shoulder and/or side wall, by repositioning or re-orienting the light source and camera so that the illumination beam of the light source and the field of view of the camera sweep the desired portion or portions of the container positioned at the inspection station.

What is claimed is:

1. Apparatus for inspecting containers comprising:
   an inspection head including means for rotating said head adjacent to a container about a fixed axis,
   a light source disposed in fixed position adjacent to said head,
   first optical transmission means on said head and aligned with said light source for receiving illumination light energy from said source and projecting said illumination energy onto the container,
   first light sensing means on said head for receiving at least a portion of said light energy following interaction of said light energy with the container and generating a first electrical signal as a function thereof,
   second optical transmission means on said head responsive to said first electrical signal for generating light energy as a function thereof,
   second light sensing means disposed in fixed position adjacent to said head in alignment with said second optical transmission means for receiving light energy generated by said second optical transmission means and generating a second electrical signal as a function thereof, and means responsive to said second electrical signal for detecting commercial variations in the container.

2. The apparatus set forth in claim 1 wherein said second optical transmission means comprises at least one optical transmitter carried by said head at a first fixed radius from said axis, and electronic means responsive to said first electrical signal for energizing said at least one optical transmitter.

3. The apparatus set forth in claim 2 wherein said second light sensing means comprises annular light sensing means concentric with said axis at a second fixed radius opposed at said at least one optical transmitter, such that optical transmission between said at least one transmitter and said annular light sensing means is independent of rotation of said head.

4. The apparatus set forth in claim 3 wherein said second optical transmission means comprises a plurality of said optical transmitters disposed in an annular array at said first fixed radius about said axis.

5. The apparatus set forth in claim 4 wherein said first and second radii are identical.

6. The apparatus set forth in claim 3 wherein said second light sensing means comprises annular optical transmission means disposed at said second radius opposed to said optical transmitter, and information processing means responsive to said second electrical signal.

7. The apparatus set forth in claim 6 wherein said information processing means includes means for generating control signals for controlling operation of said electronic means and means for transmitting said control signals through said annular optical transmission means, and wherein said electronic means includes third light sensing means carried by said head at said first fixed radius opposed to said annular light transmission means for receiving said control signals.

8. The apparatus set forth in claim 1 wherein said light source comprises first fiber optic transmission means coaxial with said fixed axis, and wherein said first optical transmission means comprises second fiber optic transmission means carried by said head in axial alignment with said first fiber optic transmission means such that said illumination lights energy is transmitted from said light source through said first and second fiber optic transmission means for projection onto the container independent of rotation of said head.

9. The apparatus set forth in claim 1 further comprising means for presenting containers in sequence for inspection and holding the containers in stationary position beneath said head coaxially with said fixed axis.

10. Apparatus for inspecting containers comprising:
an inspection head including means for rotating said head adjacent to a container about a fixed axis,
light source means on said head for projecting illumination light energy onto the container adjacent to said head,
first light sensing means on said head for receiving at least a portion of said light energy following interaction of the light energy with the container,
electronic means carried by said head and responsive to said first light sensing means for generating electrical signals as a function thereof,
at least one optical transmitter carried by said head at fixed radius to said axis and responsive to said electrical signals,
annular light sensing means at fixed radius around said axis and opposed to said at least one optical transmitter, and
means coupled to said annular light sensing means for detecting commercial variations in the container as a function of said electrical signals.

11. The apparatus set forth in claim 10 wherein said at least one optical transmitter comprises a plurality of said optical transmitters disposed in an annular array at said fixed radius about said axis.

12. The apparatus set forth in claim 10 wherein said annular light sensing means comprises annular optical transmission means, wherein said means for detecting commercial variations includes means for generating control signals for controlling operation of said electronic means and means for transmitting said signals through said annular optical transmission means, and wherein said electronic means includes light sensing means carried by said head at said fixed radius opposed to said annular light transmission means for receiving said control signals.

13. A method of inspecting containers comprising the steps of:
(a) rotating an inspection head continuously about a fixed axis adjacent to a container,
(b) generating light energy externally of said head,
(c) commutating said light energy onto said head to illuminate the container,
(d) generating optical signals on said head as a function of interaction of illumination light energy with the container,
(e) providing information processing electronics externally of said head, and
(f) commutating said optical signals off of said head to said information processing electronics.

* * * * *